United States Patent [19]

Eggler et al.

[11] Patent Number: 5,039,672
[45] Date of Patent: Aug. 13, 1991

[54] HETEROCYCLIC COMPOUNDS AS ALDOSE REDUCTASE INHIBITORS

[75] Inventors: James F. Eggler; Eric R. Larson, both of Groton, Conn.

[73] Assignee: Pfizer Inc., New York, N.Y.

[21] Appl. No.: 505,304

[22] Filed: Apr. 5, 1990

[51] Int. Cl.⁵ .............. C07D 498/10; C07D 491/107; C07D 487/10; C07D 311/96

[52] U.S. Cl. .................... 514/210; 540/203; 548/241; 548/242; 548/408; 548/410; 549/330; 549/345; 549/405; 560/31; 560/35; 560/39; 560/51; 560/53; 560/54; 560/315; 562/435; 562/462; 564/265

[58] Field of Search .................... 514/210; 540/203

[56] References Cited

U.S. PATENT DOCUMENTS

| | | | |
|---|---|---|---|
| 3,821,383 | 6/1974 | Sestanj et al. | 424/258 |
| 4,130,714 | 12/1978 | Sarges | 548/309 |
| 4,147,795 | 4/1979 | Sarges | 424/273 R |
| 4,200,642 | 4/1980 | Schnur | 424/272 |
| 4,210,663 | 7/1980 | Belletire | 424/275 |
| 4,680,388 | 7/1987 | Sundeen | 540/203 |

FOREIGN PATENT DOCUMENTS 222576 5/1987 European Pat. Off.

OTHER PUBLICATIONS

Cox, M., et al., "Spirocyclic Beta-Oxo Sulphoxides and Sulphones as Potential Aldose Reductase Inhibitors", J. Chem. Soc., Perkin Trans. I, pp. 3217–3221 (1988).

Jaspan, J., et al., "Clinical Studies with an Aldose Reductase Inhibitor in the Autonomic and Somatic Neuropathies of Diabetes", Metabolism, vol. 35, No. 4, Supp. 1, pp. 83–92 (1986).

Mattingly, P., et al., "Titanium Trichloride Reduction of Substituted N-Hydroxy-2-Azetidinones and other Hydroxamic Acids", J. Org. Chem., 45: 410–415 (1980).

Schnur, R., et al., "Spiro Oxazolidinedione Aldose Reductase Inhibitors", J. Med. Chem., 25: 1451–1454 (1982).

Graf, R., "Reactions with N-Carbonylsulfamoyl Chloride", Angew. Chem. Internat. Edit., vol. 7, No. 3, pp. 172–182 (1968).

Miller, M., et al., "Synthesis of Beta-Lactams from Substituted Hydroxamic Acids", J. Am. Chem. Soc. 102: 7026–7032 (1980).

Sarges, et al., J. Med. Chem. vol. 28, No. 11, pp. 1717–1719 (1985).

Primary Examiner—Mark L. Berch
Attorney, Agent, or Firm—Peter C. Richardson; J. Trevor Lumb; A. Dean Olson

[57] ABSTRACT

Certain spirocyclic heterocyclic compounds, and their pharmaceutically-acceptable salts, are inhibitors of the aldose reductase enzyme, and so are useful for the control of diabetic complications. Exemplary compounds include compounds of the formula

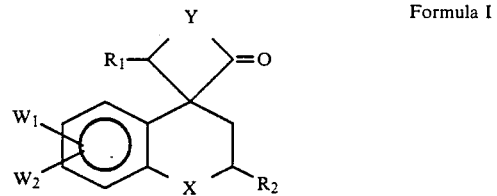

Formula I wherein Y is

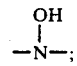

X is —O— or

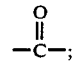

$R_1$ and $R_2$ are each independently H, alkyl $C_1$–$C_6$, aryl or arylalkyl ($C_1$–$C_6$);

$W_1$ and $W_2$ are each independently hydrogen, halogen or nitro; and the pharmaceutically acceptable base addition salts thereof.

7 Claims, No Drawings

HETEROCYCLIC COMPOUNDS AS ALDOSE REDUCTASE INHIBITORS

TECHNICAL FIELD

The field of art to which this invention relates is heterocyclic compounds which are useful in the field of medicinal chemistry. More particularly the invention relates to spirocyclic heterocylic compounds which are aldose reductase inhibitors useful for the control of diabetic complications such as neuropathy, nephropathy, retinopathy and cataractogenesis.

BACKGROUND ART

In the past, various attempts have been made by numerous investigators in the field of organic medicinal chemistry to obtain new and better oral antidiabetic agents. Many of these efforts have involved the syntheses and testing of various new and unavailable organic compounds, particularly in the area of the sulfonylureas, in an endeavor to determine their ability to lower blood sugar (i.e., glucose) levels to a substantially high degree when given by the oral route of administration. The effect of other organic compounds in preventing or arresting certain chronic complications of diabetes, such as diabetic cataracts, neuropathy and retinopathy, etc. has also been studied. For example, K. Sestanj et al. in U.S. Pat. No. 3,821,383 discloses that certain aldose reductase inhibitors like 1,3-dioxo-1H-benz[d,e]isoquinoline-2(3H)-acetic acid and some closely related derivatives thereof are useful for these purposes, even though these particular compounds are not known to be hypoglycemic in nature.

In addition, for example, commonly assigned U.S. Pat. No. 4,130,714 entitled "Hydantoin Therapeutic Agents" the disclosure of which is hereby incorporated by reference discloses dextrorotatory spiro-hydantoin compounds such as d-6-fluoro-spiro-[chroman-4,4'-imidazolidine]-2',5'-dione and d-6'-fluoro-spiroimidazolidine-4,4'-thiochroman-2,5-dione.

Non-hydantoin compounds previously reported to inhibit aldose reductase include 1H-benz[d,e]isoquinoline-1,3(2H)-dione-2-acetic acid derivatives, Sestanj et al., U.S. Pat. No. 3,821,383; halogen substituted chroman-4-carboxylic and chroman-4-acetic acids, Belletire, U.S. Pat. No. 4,210,663; spiro-[chroman-4,5'-oxazolidin]-2',3'-diones, Schnur, U.S. Pat. No. 4,200,642; and variously substituted phthalazin-1(2H)-on-4-acetic acids, Larson et al., published European Patent Application No. 222,576.

These aldose reductase inhibitors all function by inhibiting the activity of the enzyme aldose reductase, which is primarily responsible for regulating the reduction of aldoses (like glucose and galactose) to the corresponding polyols (such as sorbitol and galactitol) in the human body. In this way, unwanted accumulations of galactitol in the lens of galactosemic subjects, and of sorbitol in the lens, peripheral nervous cord and kidney of various diabetic subjects, are thereby reduced or prevented. As a result, these compounds are of value as aldose reductase inhibitors for controlling chronic diabetic complications, including but not restricted to those of an ocular nature, since it is known that the presence of polyols in an eye lens invariably leads to cataract formation and a loss of lens clarity.

Although compounds such as the hydantoins have proven useful for the treatment of diabetic complications there is a continuing search in this field of art for different, more effective inhibitors for the treatment of diabetic complications.

SUMMARY OF THE INVENTION

This invention is directed to spirocyclic heterocyclic compounds that are useful as aldose reductase inhibitors. The compounds of this invention have the formula

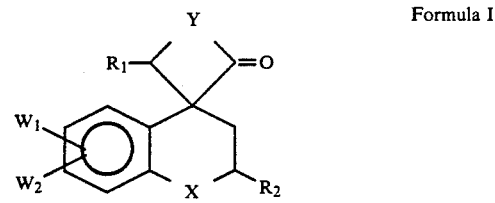

Formula I wherein
Y is

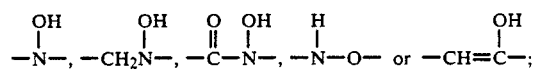

X is —O— or

$R_1$ and $R_2$ are each independently H, alkyl $C_1-C_6$, aryl or arylalkyl $C_1-C_6$;
$W_1$ and $W_2$ are each independently hydrogen, halogen or nitro; and
the pharmaceutically acceptable cationic salts thereof.

Particularly preferred are compounds of formula (I) where X is

Preferred within this group are compounds where $W_1$ is hydrogen, $W_2$ is fluorine, Y is

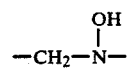

and $R_1$ and $R_2$ are each independently H or alkyl($C_1-C_6$). Preferred within this group is a compound where $R_1$ is hydrogen, $R_2$ is methyl, and fluorine is in position 6.

A second preferred group of compounds of formula (I) are those where X is —O—. Preferred within this group are compounds where Y is

$W_1$ and $W_2$ are each independently hydrogen or halogen, and $R_1$ and $R_2$ are each independently H or alkyl($C_1-C_6$) Preferred within this group are compounds where $R_1$ is hydrogen or methyl, $R_2$ is hydrogen or methyl, $W_1$ and $W_2$ are chlorine in position 6 and 7 respectively or $W_1$ is hydrogen and $W_2$ is fluorine in position 6.

Another preferred group of compounds of formula (I) where X is —O— are compounds where Y is

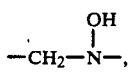
$$-CH_2-\overset{\overset{OH}{|}}{N}-,$$

$W_1$ and $W_2$ are each independently hydrogen or halogen, $R_1$ is hydrogen and $R_2$ is hydrogen, alkyl($C_1$–$C_6$) or arylalkyl($C_1$–$C_6$) Preferred within this group are compounds where $R_2$ is hydrogen, methyl, n-propyl or —$CH_2CH_2C_6H_5$ and $W_1$ and $W_2$ are chlorine in position 6 and 7 respectively or $W_1$ is hydrogen and $W_2$ is fluorine in position 6.

Another preferred group of compounds of formula (I) where X is -O- are compounds where Y is

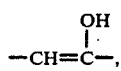
$$-CH=\overset{\overset{OH}{|}}{C}-,$$

$W_1$ and $W_2$ are each independently hydrogen or halogen, $R_1$ is hydrogen, and $R_2$ is H or alkyl ($C_1$–$C_6$). Preferred within this group are compounds wherein $R_2$ is hydrogen or methyl, $W_1$ and $W_2$ are each chlorine in position 6 and 7 respectively or $W_1$ is hydrogen and $W_2$ is fluorine in position 6.

Yet another preferred group of compounds of formula I where X is —O— are compounds where Y is

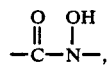
$$-\overset{\overset{O}{\|}}{C}-\overset{\overset{OH}{|}}{N}-,$$

$W_1$ and $W_2$ are each independently hydrogen or halogen and $R_1$ and $R_2$ are hydrogen.

Yet another preferred group of compounds of formula I where X is —O— are compounds where Y is

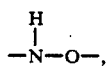
$$-\overset{\overset{H}{|}}{N}-O-,$$

$W_1$ and $W_2$ are each independently hydrogen or halogen and $R_1$ and $R_2$ are hydrogen.

The present invention is also directed to pharmaceutical compositions for the control of chronic diabetic complications in mammals which comprise a compound of the formula (I) in a pharmaceutically acceptable carrier; and to a method of controlling chronic diabetic complications which comprises administering to a mammal suffering from chronic diabetes a chronic diabetic complication controlling amount of a compound of the formula (I).

Other features and advantages will be apparent from the specification and claims.

DETAILED DESCRIPTION OF THE INVENTION

The compounds of this invention may be made using the appropriate (appropriately substituted to achieve the desired $W_1$, $W_2$, X and $R_2$ functionalities) compound of formula II illustrated empirically below, as starting material:

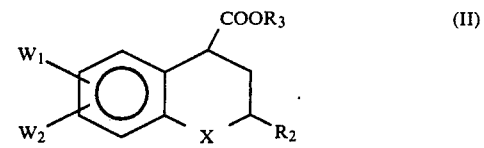

where $W_1$, $W_2$ are hydrogen, nitro or halogen; X is oxygen or carbonyl; $R_2$ is H, alkyl ($C_1$–$C_6$), aryl or arylalkyl ($C_1$–$C_6$) and $R_3$ is alkyl ($C_1$–$C_6$) or arylalkyl. Aryl as used herein is defined as including for example, phenyl and phenyl substituted with chlorine, methoxy, etc. Halogen as used herein is defined as chlorine, bromine, fluorine or iodine.

The above described ester compounds of formula II where X is —O— may be produced from the corresponding 2,3-dihydro-4H-benzopyran-4-one (appropriately substituted to achieve the desired $W_1$, $W_2$ and $R_2$ functionalities) according to Example 1. The desired 2,3-dihydro-4H-benzopyran-4-one starting compound may be produced according to the following reaction sequence and as exemplified in Example 11. Phenol (appropriately substituted to achieve the desired $W_1$, $W_2$ substitutents) is heated to reflux with an acrylonitrile (appropriately substituted to achieve the desired $R_2$ substituent) and Triton B (N-benzyltrimethylammonium hydroxide) for over 35 hours to produce the desired phenoxy propionitrile. The phenoxy propionitrile is hydrolyzed under acidic conditions to the corresponding carboxylic acid. The carboxylic acid is cyclized to the ketone by acid treatment at 50° C. for 15–45 minutes followed by quenching with water. (J. Med. Chem., 28, 1716 (1985)). The phenol and acrylonitrile starting compounds can be easily synthesized by those skilled in the art starting from common chemical reagents using conventional methods of organic synthesis.

When X is carbonyl, the above described ester compounds of formula II may be produced according to the following sequence. A phenylacetate ester (appropriately substituted to achieve the desired $W_1$ and $W_2$ functionality) is reacted with a methacrylate (appropriately substituted to achieve the desired $R_2$ functionality) under basic catalysis, for example, tertbutoxide in N,N-dimethylformamide. The resulting diester is saponified to the corresponding diacid which is then cyclized under acidic conditions to yield the ketone carboxylic acid. The carboxylic acid function is then esterified under acidic conditions to yield the desired tetralone-4-carboxylic acid ester.

In general, for the production of compounds of formula I in which Y is

$$-\overset{\overset{OH}{|}}{N}-,$$

the above described ester compounds of formula II undergo an aldol reaction (utilizing the appropriate aldehyde to achieve the desired $R_1$ functionality in Formula I) to yield the desired hydroxy ester (III) as described empirically below:

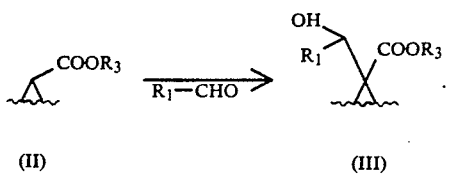

(II)          (III)

Preferably the ester is reacted with a strong base such as a sterically hindered amide ion (e.g., lithium diisopropylamide) at temperatures below about −66° C. to achieve anion formation. The resulting intermediate is reacted with the desired aldehyde at temperatures below about −66° C. Typically an aprotic solvent such as THF is used.

The beta-hydroxy ester (III) thus obtained is hydrolyzed to the corresponding hydroxy acid (IV) as described empirically below:

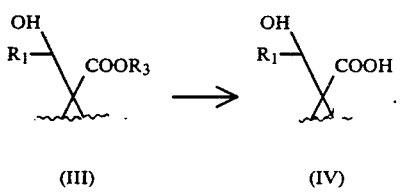

(III)          (IV)

Preferably the ester is saponified to the carboxylic acid. It is especially preferred that the ester is heated with a base such as sodium hydroxide in aqueous methanol to effect hydrolysis. The beta-hydroxy acid is isolated after acidification to pH 3–6.

Alternatively, when $R_3$ is benzyl, the beta-hydroxy acid is obtained by hydrogenolysis. This reaction sequence reduces an undesired retro aldol reaction that can occur in the above described saponification sequence because it eliminates the need for basic reaction conditions.

The hydroxy acid (IV) (from either of the above reaction sequences) is converted to the corresponding hydroxamic acid (V) by coupling with an O-substituted hydroxylamine such as O-benzylhydroxylamine in the presence of a carbodiimide. This yields the O-substituted hydroxamic acid as described empirically below:

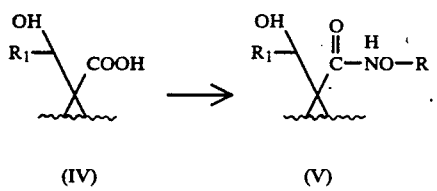

(IV)          (V)

where R is an alkyl group such as benzyl or methyl. Preferably the hydroxyacid is reacted with O-benzylhydroxylamine and 1-ethyl-3-(3-dimethylaminopropyl)-carbodiimide in a protic solvent system such as aqueous DMF at a pH of about 3.5 to about 5.5 because within that pH range coupling is facilitated.

The O-substituted beta-hydroxyhydroxamic acid (V) thus obtained is then acylated to yield the corresponding sulfonate ester (VI) as described empirically below:

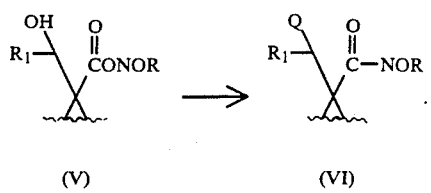

(V)          (VI)

where Q is $CH_3SO_3-$.

Preferably the sulfonate ester of the alcohol is made by reaction with a sulfonyl chloride in pyridine at temperatures below about room temperature.

The sulfonate ester (VI) is then cyclized (i.e., lactamized) to the corresponding N-alkoxy beta-lactam (VII) as described empirically below:

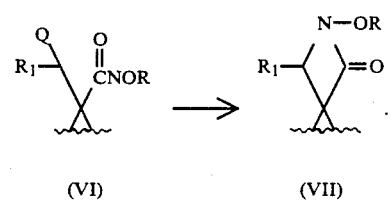

(VI)          (VII)

Preferably the sulfonate ester is heated at reflux with a base such as potassium carbonate to eliminate methanesulfonic acid and yield the N-alkoxy beta-lactam.

When R equals phenylmethyl the N-benzylozy beta-lactam (VIII) undergoes hydrogenolysis as described empirically below to yield the corresponding desired end product, the N-hydroxy beta-lactam (VIII):

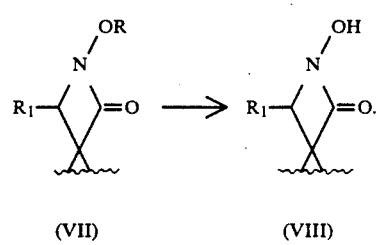

(VII)          (VIII)

Preferably the benzyl ether and a noble metal catalyst are stirred in a hydrogen atmosphere at ambient temperatures in protic solvents such as alcohol at elevated pressures such as 5–50 psi.

In general for the production of compounds of formula I in which Y is

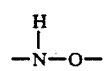

the above described N-hydroxy beta-lactam (VIII) undergoes an acid catalyzed rearrangement as described empirically below to yield the corresponding isoxazolidin-5-one (IX):

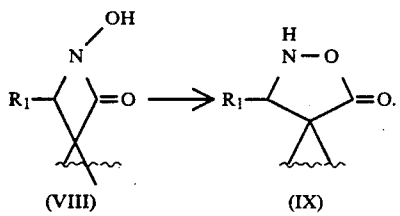

(VIII) → (IX)

Preferably a solution of the N-hydroxy lactam in a protic solvent containing a catalytic amount of acid is stirred at ambient temperature to affect the rearrangement.

For the production of compounds of formula I in which Y is

(the cyclopentanedione functionality) the following reaction sequence is typically used. The ester (II) (appropriately substituted to achieve the desired $W_1$, $W_2$, X, and $R_2$ functionalities) is alkylated using the bromo ester (appropriately substituted to achieve the desired $R_1$ substituent) to yield the desired dicarboxylic acid ester (X) as described empirically below:

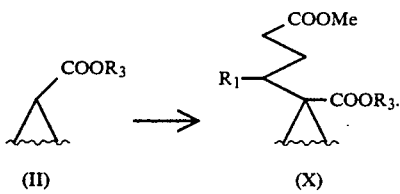

(II) → (X)

Preferably the methyl ester is reacted with a base such as sodium hydride at ambient conditions to affect anion formation and then the appropriate methyl ester halide is added.

The diester (X) is then subjected to Dieckmann cyclization conditions to yield the corresponding beta-keto-ester (XI) as described empirically below:

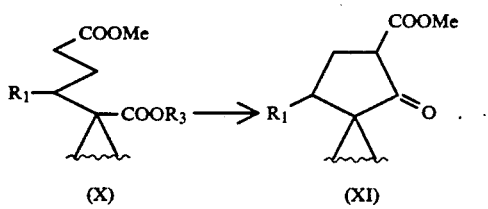

(X) → (XI)

Preferably, the diester is reacted with a base such as NaH, at ambient conditions in solvents such as DMF, THF, or dioxane and then acidified to a pH about 4–6 to facilitate product isolation.

The beta-keto ester (XI) undergoes a hydrolysis and decarboxylation as described empirically below to yield the corresponding cyclopentanone (XII):

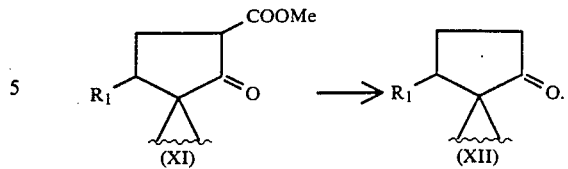

(XI) → (XII)

Preferably the beta-keto ester is refluxed with acid.

The cyclopentanone (XII) undergoes an oximation as described empirically below to yield the cyclopentanone oxime (XIII):

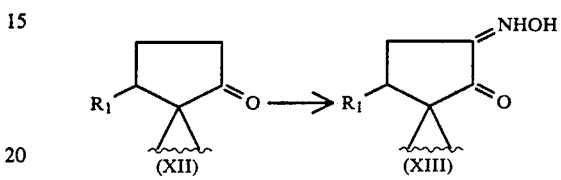

(XII) → (XIII)

Preferably the cyclopentanone is reacted at temperatures −30° C. to about 0° C. with an alkyl nitrate and a base in an aprotic solvent.

The cyclopentanone oxime (XIII) undergoes an acid catalyzed hydrolysis as described empirically below to yield the desired end product cyclopentanedione (XIV):

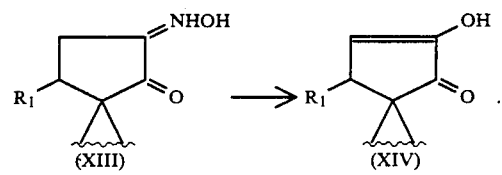

(XIII) → (XIV)

Preferably, the cyclopentanone oxime is refluxed with aqueous acid.

In general for the production of compounds of formula I in which Y is

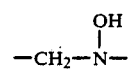

the following reaction sequence is typically utilized. The appropriately substituted 2,3-dihydro-4H-benzopyran-4-carboxylate ester (II) (i.e., substituted to achieve the desired $W_1$, $W_2$, X, and $R_2$ functionality) undergoes an allylation to yield the desired alkylated ester (XV) as described empirically below:

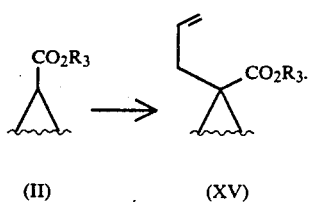

(II) → (XV)

Preferably the carboxylate ester is dissolved in a polar aprotic solvent such as anhydrous N,N-dimethylformamide and added to a base such as sodium hydride under an inert gas. The reaction mixture is typically cooled to avoid an uncontrolled exotherm and the appropriate allylic halide is added to achieve the desired R₁ substituent.

The allylic substituent is then oxidized to an aldehyde, the oxime is formed and reduced to the hydroxylamine (XVI) as described empirically below:

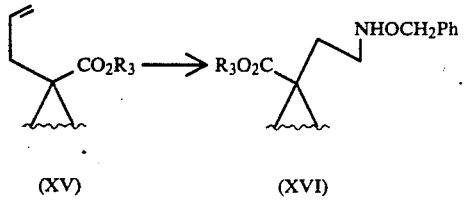

(XV)     (XVI)

Preferably, the allylic substituent is oxidized to the aldehyde with a selective oxidant (to avoid oxidation to the carboxylic acid) (e.g., ozone at low temperature). Preferably the aldehyde is converted to the corresponding oxime by reaction with a hydroxylamine, preferably O-substituted (e.g., O-benzylhydroxyamine), using mild acid or base catalysis. The O-substitution facilitates the ring closure described below. The oxime is reduced under mild conditions to avoid reduction to the amine (e.g., sodium cyanoborohydride with acidic catalysis).

The hydroxylamine derivative (XVI) is then cyclized (condensed) to yield the 5 membered lactam (XVII). Alternatively, the benzyl ester, benzyl 6-fluoro-2-methyl2,3-dihydro-4H)-benzopyran-4-carboxylate, could have been utilized in place of the methyl ester. This results in two diastereomeric 5 membered lactam compounds which may be separated:

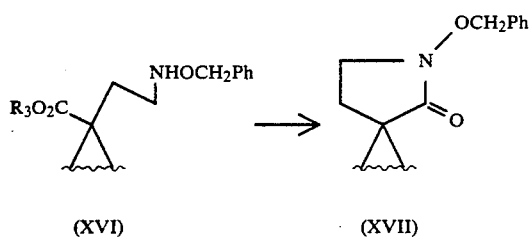

(XVI)     (XVII)

Preferably, the lactam is reacted with a strong base such as a sterically hindered amide ion (e.g., lithium diisopropylamide) at temperatures below about 0° C. Typically an aprotic solvent such as THF is used. Then the solution is acidified and the product isolated.

In those cases where the protecting group is used it is removed at this point for example, for the case of the O-benzyl ether (XVII), by hydrogenolysis to yield the desired end product N-hdyroxylactam (XVIII) functionality as described empirically below:

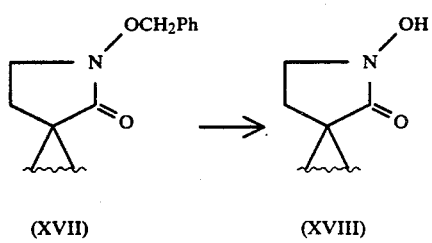

(XVII)     (XVIII)

Preferably the protecting group is removed under conditions where the product hydroxy lactam is stable. For example, the O-benzyl protecting group is cleaved with hydrogen in the presence of a suitable noble metal supported catalyst.

In general for the formation of compounds of formula I in which Y is

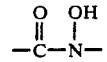

(the N-hydroxyimide functionality) the following reaction sequence is typically utilized. The appropriately substituted 2,3-dihydro-4H-benzopyran-4-carboxylate (II) (i.e., substituted to achieve the desired W, X and R₂ functionality) is alkylated and hydrolyzed to the corresponding diacid (XIX) as described empirically below:

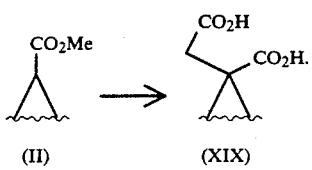

(II)     (XIX)

Preferably the carboxylate is dissolved in a polar aprotic solvent such as anhydrous N,N-dimethyl formamide and added to a base such as sodium hydride. The reaction mixture is typically cooled to avoid uncontrolled exotherm and the appropriate alkyl haloacetate (e.g., to achieve the desired R₁ ethyl bromoacetate) is added to yield the desired diester. The diester is hydrolyzed under basic conditions to yield the diacid.

The diacid (XIX) is then cyclized to the anhydride, which is reacted to form the hydroxamic acid-carboxylic acid which is dehydrated to form the desired N-hydroxylimide (XX) functionality as described empirically below

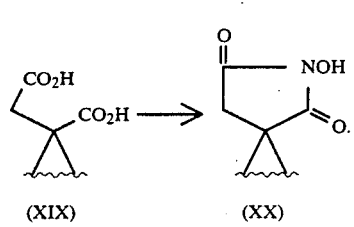

(XIX)     (XX)

Preferably the diacid is dehydrated (e.g., reaction with acetic anhydride under reflux) to yield the anhydride. The anhydride is reacted with hydroxylamine in an alcohol and ambient temperatures to yield the hydroxamic acid-carboxylic acid. The hydroxamic acid-carboxylic acid is then dehydrated by for example heating in an inert solvent to form the desired hydroxylimide.

The expression used herein, "pharmaceutically acceptable cationic salt", refers to non-toxic salts.

Thus, the compounds of this invention are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. For example the cation may be (but is not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The compounds of this invention are all readily adapted to therapeutic use as aldose reductase inhibitors for the control of chronic diabetic complications in mammals. They are administered either orally or parenterally, or topically as eye drops, in dosages ranging from about 0.1 to 20 mg/kg of body weight per day in single or divided doses. Of course, in particular situations, at the discretion of the attending physician, doses outside of this range will be used.

The compounds of this invention can be administered in a wide variety of different dosage forms, i.e., they may be combined with various pharmaceutically-acceptable inert carriers in the form of tablets, capsules, lozenges, troches, hard candies, powders, sprays, elixirs, syrups, injectable or eye drop solutions, and the like. Such carriers include solid diluents or fillers, sterile aqueous media and various non-toxic organic solvents.

For purposes of oral administration, tablets containing various excipients such as sodium citrate, calcium carbonate and calcium phosphate are employed along with various disintegrants such as starch and preferably potato or tapioca starch, alginic acid and certain complex silicates, together with binding agents such as polyvinylpyrrolidone, sucrose, gelatin and acacia Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the essential active ingredient therein can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitably buffered, if necessary, and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of topical administration, dilute, sterile, aqueous solutions (usually in about 0.1% to 5% concentration), otherwise similar to the above parenteral solutions, are prepared in containers suitable for dropwise administration to the eye, this being particularly advantageous for enhancing delivery to this organ.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

The compounds of this invention are useful for the control of diabetic complications. The activity can be determined by, for example, the concentration that causes 50% inhibition of partially purified human placenta aldose reductase using glyceraldehyde as a substrate following the procedure described in U.S. Pat. No. 3,821,383 and based on the procedure of Hayman et al., Journal of Biological Chemistry, 240, 877 (1965). The substrate employed is partially purified aldose reductase enzyme obtained from human placenta.

Activity can also be determined by, for example, the oral dose which inhibits sorbitol accumulation in sciatic nerves of streptozotocized rats by 50% by a procedure essentially as described in U.S. Pat. No. 3,821,383. The amount of sorbitol accumulation in the sciatic nerves was measured 27 hours after induction of diabetes. The compounds were generally administered orally at doses ranging from 2.5 to 100 mg/kg at 4, 8 and 24 hours following the administration of streptozotocin. The results obtained compared to the case where no compound was administered (i.e., the untreated animal where sorbitol levels normally rise from approximately 50–100 mM/g tissue to as high as 400 mM/g tissue during the test period). Although, not all of the compounds of the present invention show in vivo activity by this oral test those compounds will find parenteral or topical use.

EXAMPLE 1

1. 6-fluoro-2,3-dihydro-4-cyano-4-[(trimethylsilyl)oxy]-4H-benzopyran

To a solution of 20 g (0.12 moles) of 2,3-dihydro-6-fluoro-4H-benzopyran-4-one (prepared from 4-fluorophenol and acrylonitrile as described in J. Med. Chem., 28, 1716 (1985) and 23 mL (0.18 moles) of trimethylsilyl cyanide in 220 mL of $CH_2Cl_2$ was added 500 mg of zinc iodide. The reaction was stirred at room temperature for 20 hours then poured onto ice-water. The $CH_2Cl_2$ layer was washed with water, 10% aqueous $NaHCO_3$ and brine then dried over $MgSO_4$, filtered and evaporated to give 32 g of crude product which was used without purification.

2. 6-fluoro-4-cyano-2H-benzopyran

To a solution of 32 g (0.12 mole) of the crude 6-fluoro-2,3-dihydro-4-cyano-4-[(trimethylsilyl)oxy-]4H-benzopyran in 170 ml of dry pyridine was added 60 ml (0.6 mole) of phosphorous oxychloride. The reaction was heated to reflux for 5 hours then cooled to room temperature. The resulting solution was added dropwise to a solution of 300 cc of concentrated HCl in 1 L of water. This aqueous layer was extracted with EtOAc and the EtOAc layer was dried over $Na_2SO_4$, filtered and evaporated to give 16.1 g of product m.p. 114°–115° C. NMR ($CDCl_3$) ppm (delta) 5.00 (d, 2H, J=4 Hz), 6.6–7.3 (m, 4H).

3. 6-fluoro-2,3-dihydro-4-cyano-4H-benzopyran

To a solution of 16.1 g (0.092 moles) of 6-fluoro-4-cyano-2H-benzopyran in 270 mL of absolute methanol was added 5.52 g (0.23 mole) of magnesium turnings. The resulting exothermic reaction was allowed to reflux then stirred at room temperature for 2 hours. The volatiles were evaporated and the residue dissolved in water which was acidified to pH 2.0 with concentrated HCl. The aqueous was extracted with EtOAc and the EtOAc layer was dried over Na$_2$SO$_4$, filtered and evaporated to give 16 g of crude product. The crude aproduct was purified by chromatography and 450 g of silica gel eluting with CH$_2$Cl$_2$/ether to give 9 g of product m.p. 67°-68° C. NMR CDCl$_3$ ppm (delta): 2.25 (dt, 2H, J=5 Hz), 4.95 (s, 1H, J=5 Hz), 4.00-4.30 (m, 2H), 6.70-7.05 (m, 3H). 4. 6-fluoro-2,3-dihydro-4H-benzopyran-4-carboxylic acid A solution of 8.5 g 0.05 moles) of 6-fluoro-2,3-dihydro-4-cyano-4H-benzopyran and 21.8 g (0.39 moles) of KOH in 250 ml of ethylene glycol was stirred and heated at 170° C. overnight.

The reaction was cooled and poured into water, acidified to pH 1 by the addition of concentrated HCl and extracted with EtOAc. The EtOAc layer was dried over Na$_2$SO$_4$, filtered and evaporated to give 8.4 g of product m.p. 111°-115° C.

5. Methyl 6-fluoro-2,3-dihydro-4H-benzopyran-4-carboxylate

A solution of 8.4 g of the 6-fluoro-2,3-dihydro-4H-benzopyran-4-carboxylic acid in 580 mL of methanol was perfused with HCl gas for 5 minutes. The resulting solution was stirred at room temperature overnight. The volatiles were evaporated and the residue dissolved in ether. The ether layer was washed with water then dried over Na$_2$SO$_4$, filtered and evaporated to give 8.7 g of crude product which was purified by chromatography on 300 g of silica gel eluting with CH$_2$Cl$_2$ to give 6.2 g of product as an oil. NMR (CDCl$_3$) ppm (delta): 2.00-2.40 (m, 2H), 3.80 (s, 3H), 2.5 (t, 1H, J=4 Hz), 7.10-6.70 (m, 3H).

EXAMPLE 2

1. Methyl 6-fluoro-3,4-dihydro-4-(hydroxymethyl)-2H-benzopyran-4-carboxylate

A solution of 5 mL (0.035 mole) of diisopropylamine in 100 mL of THF was cooled to 0° C. and 22.1 mL (0.35 mole) of 1.6M butyllithium in hexane was added dropwise. After stirring for 30 minutes at 0° C. the resulting solution was cooled to −78° C. A solution of 6.2 g (0.0295 mole) of Methyl 6-fluoro-2,3-dihydro-4H-benzopyran-4-carboxylate in 20 mL of THF was then added dropwise while maintaining the temperature below −66° C. The resulting solution was stirred at −78° C. for 3 hours. Gaseous formaldehyde was then bubbled into the solution for 5 minutes. The reaction was allowed to warm to room temperature, then diluted with water and extracted with EtOAc. The EtOAc layer was dried over Na$_2$SO$_4$, filtered and evaporated to give 7.6 g of crude product as an oil. NMR (CDCl$_3$) ppm (delta): 2.20-2.60 (m, 2H), 3.8 (s, 3H), 4.26 (t, 2H, J=5 Hz), 4.90 (m, 2H), 6.80-7.20 (m,3H).

| Mass spectrum: | calc'd for C$_{12}$H$_{13}$O$_4$F | 240.0802 |
| --- | --- | --- |
| | found | 240.0777 |

2. 6-fluoro-3,4-dihydro-4-(hydroxymethyl)-2H-benzopyran-4-carboxylic acid

To a solution of 7 g (0.029 mole) Methyl 6-fluoro-3,4-dihydro-4-(hydroxymethyl)-2H-benzopyran-4-carboxylate in 200 mL of McOH was added 7.2 mL of 5N NaOH. The reaction was heated on a steam bath overnight then cooled to room temperature. The MeOH was evaporated and the residue dissolved in water then acidified to pH 4.0 with concentrated HCl. The aqueous was extracted with EtOAc and the EtOAc layer was dried over Na$_2$SO$_4$, filtered and evaporated to give 6 g of crude product. Chromatography on 160 g of silica gel eluting with CH$_2$Cl$_2$/ether gave 2.7 g of product, m.p. 134°-135° C.

| Mass spectrum: | calc'd for C$_{11}$H$_{11}$O$_4$F | 226.0642 |
| --- | --- | --- |
| | found | 226.0646 |

3. 6-fluoro-3,4-dihydro-4-(hydroxymethyl)-2H-benzopyran-4-carboxylic acid 6-fluoro-3,4-dihydro-4-(hydroxymethyl)-2H-benzopyran-4-carboxylic acid 1.99 g (0.0088 moles) was dissolved in 25 mL of H$_2$O/DMF (4/1). O-Benzylhydroxylamine hydrochloride 2.8 g (0.0176 moles) was dissolved in 60 mL of water and the pH of this solution was adjusted to 4.5 by addition of 50% NaOH solution. This solution was then added dropwise to the hydroxy acid solution. After adjusting the pH of the reaction mixture to pH 4.5, a solution of 3.36 g (0.0176 mole) of 1-ethyl-3-(3-dimethylaminopropyl)carbodimide in 40 mL of H$_2$O was added dropwise while adjusting the pH of the reaction mixture to 4.5 by addition of 1N HCl. The reaction was stirred at room temperature for 1 hour then diluted with water and extracted with EtOAc. The EtOAc layer was dried over Na$_2$SO$_4$, filtered and evaporated to give 3.8 g crude product. Chromatography on silica gel eluting with CH$_2$Cl$_2$/Et$_2$O gave 3.0 g of product. NMR (CDCl$_3$) ppm (delta): 2.00-2.40 (m, 2H), 3.60-4.35 (m, 6H), 4.90 (s, 2H), 6.80-7.10 (m, 3H), 7.40 (s, 5H).

4. 6-fluoro-3,4-dihydro-4-(methanesulfonyloxymethyl)-2H-benzopyran-4-N-(phenylmethoxy)-carboxamide To a solution of 2.9 g (0.0088 moles) of 6-fluoro-3,4-dihydro-4-(hydroxymethyl)-2H-benzopyran-4-N-(phenylmethoxy)-carboxamide in 60 mL of pyridine was cooled to 0° C. and 2 g (0.0176 moles) of methanesulfonylchloride was added dropwise. The reaction is allowed to warm to room temperature and stirred overnight. The reaction was poured into 400 mL of H$_2$O/1NHCl (1/1). The resulting aqueous was then extracted with EtOAc. The EtOAc extracts were dried over Na$_2$SO$_4$, filtered and evaporated to give 3.7 g of crude product which was used without purification.

5. 6'-fluoro-2',3'-dihydro-4-phenylmethoxy-Spiro-[azetidine-3,4'-[4H-benzopyran]-2-one To a suspension of 3.6 g (0.026 moles) of potassium carbonate in 100 mL of acetone was added 3.6 g (0.0088 moles) of 6-fluoro-3,4-dihydro-4-(methanesulfonyloxymethyl)-2H-benzopyran-4-N-(phenylmethoxy)-carboxamide. The reaction was heated at reflux for 3 hours then cooled to room temperature and filtered. The filtrate was evaporated and the residue dissolved in EtOAc. The EtOAc layer was washed with H$_2$O, dried over Na$_2$SO$_4$ and filtered to give 2.5 g of product, m.p. 60°-64° C.

| Mass spectrum: | calc'd for $C_{18}H_{16}NFO_3$ | 313.1101 |
| --- | --- | --- |
| | found | 313.1123 |

6.
6'-fluoro-2',3',dihydro-1-hydroxy-spiro[azetidin-3,4'-[4H-benzopyran]-2-one To a solution of 2.48 g (0.0079 moles) of the 6'-fluoro-2',3'-dihydro-1-phenylmethoxy-spiro[azetidine-3,4'-[4H-benzopyran]-2-one in 150 ml of methanol was added 500 mg of 10% Pd of charcoal. The reaction was stirred in a hydrogen atmosphere until $N_2$ uptake ceased. The reaction was filtered and the filtrate evaporated to give the product which was recrystallized from $CH_2Cl_2$ to give 600 mg of product, m.p. 160°–161° C.

| Mass spectrum: | calc'd for $C_{11}H_{10}NO_3F$ | 223.0644 |
| --- | --- | --- |
| | found | 223.0661 |

6',7'-dichloro-2',3'-dihydro-1-hydroxy-spiro-[azetidin-3,4'-benzopyran]-2-one (m.p. 157°–158° C.) was prepared in an analogous fashion to Example 2 above, starting from benzyl 6,7-dichloro-4H-1-benzopyran-4-carboxylate by the same procedure as Example 2, via intermediacy of: benzyl 4-(hydroxymethylene)-6,7-dichloro-4H-1-benzopyran-4-carboxylate (Rf=0.3 (1:1 diethylether/hexanes, $SiO_2$), N-benzyloxy-4-(hydroxymethylene)-6,7-dichloro-4H-1-benzopyran-4-carboxamide (Rf=0.3 diethylether, $SiO_2$), N-benzyloxy-4-(methanesulfonoxymethylene)-6,7-dichloro-4H-1-benzopyran-4-carboxamide (Rf=0.3, 2:1 dichloromethane/ethyl acetate, $SiO_2$), 1'-benzyloxy-2,3-dihydro-6,7-fluoro-spiro-(4H-1-benzopyran-4,3'-azetidine)-2'-one (Rf=0.7, 2:1 dichloromethane/ethyl acetate).

The less polar diastereomer of 6'-fluoro-2',3'-dihydro-2'-methyl-1-hydroxy-spiro[azetidin-3,4'-benzopyran]-2-one (mp 173°–174°) and the more polar diastereomer of 6'-fluoro-2',3'-dihydro-2'-methyl-1-hydroxy-spiro [azetidin-3,4'-benzopyran]-2-one (m.p. 118°–120° C.) were prepared in an analogous fashion to Example 2 above from 6-fluoro-2,3-dihydro-2-methyl-4H-benzopyran-4-one. The diastereomers were separated by column chromatography on silica gel.

The less polar diastereomer of 6'-fluoro-2',3'-dihydro-1-hydroxy-4-methyl-spiro[azetidin-3,4'-benzopyran]-2-one (m.p. 173°–174°) and the more polar diastereomer of 6'-fluoro-2',3'-dihydro-1-hydroxy-4-methyl-spiro[azetidin-3,4'-benzopyran]-2-one (m.p. 178°–180° C.) were also made in analogous fashion to Example 2 above, except acetaldehyde was used in place of formaldehyde in Part 1 of Example 2.

The diastereomers were separated by column chromatography on silica gel.

EXAMPLE 3
6-fluoro-2,3-dihydro-spiro[4H-1-benzopyran-4,4'-isoxazolidin]-5'-one In a 50 cc R.B. flask fitted with magnetic stirring was placed 30 cc of absolute ethanol, this was perfused with HCl gas for 10 minutes (saturated), this solution was allowed to cool to room temperature and 120 mg of 6'-fluoro-2',3'-dihydro-1-hydroxy-spiro-[azetidine-3,4'-[4H-benzopyran]-2-one in 3 cc of ethanol was added in one portion, the reaction was allowed to stir at room temperature for 60 minutes, then evaporated to a residue which was recrystallized from hexane/$CH_2Cl_2$ to give 52 mg of product (m.p. 153°–155°).

EXAMPLE 4
1. Methyl 6-Fluoro-3,4-dihydro-4-(methoxycarbonyl)-2H-benzopyran-4-butanoate To a suspension of 8.81 g (0.183 mol) 50% NaH in 300 ml of DMF was added, dropwise, a solution of 27.5 g (0.131 mol) of methyl 6-fluoro-2,3-dihydro-4H-benzopyran-4-carboxylate in 100 ml of DMF. After stirring at room temperature for 1 hour, a solution of 33 g (0.183 mol) of methyl 4-bromobutyrate in 25 ml of DMF was added. The resultant homogeneous solution was stirred at room temperature for 16 hours and then poured onto ice/$H_2O$ and acidified to pH 3.0 with concentrated HCl. The aqueous was extracted twice with $CH_2Cl_2$ and the combined extracts were dried ($NaSO_4$) and filtered. The filtrate was evaporated in vacuo to an oil (44 g) which was purified by column chromatography on 2 Kg of silica gel, eluting with $CH_2Cl_2/Et_2O$. Yield 12 g (30%), an oil; NMR ($CDCl_3$) (delta) 1.5–2 6(m, 8H, $CH_2$), 3.62 (s, 3H, $CH_3$), 3.66 (s, 3H, $CH_3$), 4.21 (t, 2H, J=6 Hz, $CH_2$), 6.7–7.4 (m, 3H, arom).

| Mass spectrum: | calc'd for $C_{16}H_{19}O_5F$ | 310.1216 |
| --- | --- | --- |
| | found | 310.1184 |

2. Methyl 6-fluoro-2,3-dihydro-2'-oxo-spiro[4H-benzopyran-4,1'-cyclopentane]-3'-carboxylate To a suspension of 4.02 g (0.084 mol) of 50% NaH in 200 ml of DMF was added dropwise a solution of 11.8 g (0.089 mol) of methyl 6-fluoro-3,4-dihydro-4-(methoxycarbonyl)-2H-benzopyran-4-butanoate. The resultant homogeneous solution was stirred at room temperature for 16 hours and then poured onto ice/$H_2O$ and acidified to pH 3.0 with concentrated HCl. The aqueous was extracted twice with EtOAc and the combined extracts were dried ($NaSO_4$) and filtered. The filtrate was evaporated in vacuo to a solid residue (10.6 g, 100%), which was recrystallized from $CH_2Cl_2$/hexane m.p. 80°–83° C. The compound gave a positive FeCl test. NMR ($CDCl_3$) (delta) 1.6–2.8 (m, 6H, $CH_2$), 3.8 (s, 3H, $CH_3$), 4.0–5.5 (m, 2H, $CH_2$), 6.6–6.9 (m, 3H, arom), 10.4 (s, 1H, OH).

| Mass spectrum: | calc'd for $C_{15}H_{15}O_4F$ | 278.0955 |
| --- | --- | --- |
| | found | 278.0955 |

3.
6-fluoro-2,3-dihydro-2'-oxo-spiro[4H-benzopyran-4,1'-cyclopentane]

A mixture of 10.6 g (0.038 mol) of Methyl 6-fluoro-2,3-dihydro-2'-oxo-Spiro[4H-benzopyran-4,1'-cyclopentane]-3'-carboxylate in 280 ml of 1N HCl containing 8 ml of concentrated HCl was heated at reflux for 3 hours. The reaction was cooled to room temperature and extracted twice with EtOAc. The combined extracts were dried over $NaSO_4$ and filtered. The filtrate was evaporated in vacuo to a solid residue (5.7 g, 68%) which was recrystallized from petroleum ether:

m.p. 49°–51° C. NMR (CDCl₃) (delta) 1.7–2.7 (m, 8H, CH₂), 4.0–4.5 (m, 2H, CH₂), 6.4–6.9 (m, 3H, arom).

4. 6-fluoro-2,3-dihydro-spiro[4H-benzopyran-4,1′-cyclopenten]-2′,3′-dione,3′-oxime A solution of 8.6 g (0.039 mol) of 6-fluoro-2,3-dihydro-2′-oxo-Spiro[4H-benzopyran-4,1′-cyclopentane] and 5.5 g (0.047 mol) of isoamyl nitrate in 200 ml of THF was cooled to 0° C. A suspension of 5.25 g of potassium t-butoxide in 50 ml of THF was then added portionwise keeping the temperature below 5° C. The reaction was stirred at 0° for 5 minutes then poured into water and acidified to pH 3.5 with HOAc. The aqueous was extracted twice with EtOAc and the combined extracts were dried (NaSO₄) and filtered. The filtrate was evaporated in vacuo to a solid residue (6.2 g, 64%) which was recrystallized from CH₂Cl₂/hexane: m.p. 170°–172° C.; NMR (CDCl₃) (delta) 1.8–3.2 (m, 6H, CH₂), 4.0–4.3 (m, 2H, CH₂), 6.5–6.9 (m, 3H, arom).

| Mass spectrum: | calc'd for C₁₃H₁₂NO₃F | 249.0801 |
| --- | --- | --- |
| | found | 249.0819 |

5. 6-fluoro-2,3-dihydro-3′-hydroxy-spiro[4H-benzopyran-4,1′-[3]cyclopenten]-2′-one A solution of 5.6 g (0.022 mol) of 6-fluoro-2,3-dihydro-Spiro[4H-benzopyran-4,1′-cyclopenten]-2′,3′-dione, 3′-oxime in 50 ml of acetone and 50 ml of 1N HCl was heated at reflux for 30 hours. The resultant solution was poured onto ice/H₂O and extracted twice with EtOAc. The combined extracts were dried (NaSO₄) and filtered. The filtrate was evaporated in vacuo to a solid residue which was recrystallized from CH₂Cl₂/hexane to give 2.6 g of product m.p. 172°–173° C.; IR(KBr) 3350, 1695cm⁻1; NMR (acetone-d6) (delta) 1.8–2.2 (m, 2H, CH₂), 3.8–4.6 (m, 2H, CH₂), 6.4–7.0 (m, 4H, arom and CH), 7.8–8.6 (s, 1H, OH).

| Mass spectrum: | calc'd for C₁₃H₁₁O₃F | 234.0692 |
| --- | --- | --- |
| | found | 234.0699 |

The less polar diastereomer of 6,7-dichloro-2,3-dihydro-2-methyl-3′-hydroxy-spiro[4H-benzopyran-4,1′-[3]cyclopenten]-2′-one (m.p. 158°–160°) and the more polar diastereomer of 6,7-dichloro-2,3-dihydro-2-methyl-3′-hydroxy-spiro[4H-benzopyran-4,1′-[3]cyclopenten]-2′-one (m.p. 208°–210°) were prepared in an analogous fashion to Example 3 from methyl 6,7-dichloro-2,3-dihydro-2-methyl-4H-benzopyran-4-carboxylate. The diastereomers were separated by column chromatography on silica gel.

The less polar diastereomer of 6-fluoro-2,3-dihydro-2-methyl-3′-hydroxy-spiro[4H-benzopyran-4,1′-[3]cyclopent]-2′-one (m.p. 147°–148°) and the more polar diastereomer of 6-fluoro-2,3-dihydro-2-methyl-3′-hydroxy-spiro[4H-benzopyran-4,1′-[3]cyclopent]-2′-one (m.p. 149°–150°) were prepared in an analogous fashion to Example 3 from methyl 6-fluoro-2,3-dihydro-2-methyl-4H-benzopyran-4-carboxylate. The enantiomers were separated by column chromatography on silica gel.

EXAMPLE 5

1. Methyl 2,3-dihydro-6-fluoro-4-(2-propenyl)-4H-1-benzopyran-4-carboxylate

A solution of methyl 6-fluorochromane-4-carboxylate (2.1 g) in anhydrous N,N-dimethylformamide was added to a suspension of sodium hydride (265 mg) in anhydrous N,N-dimethylformamide under nitrogen. After gas evolution ceased, the mixture was cooled to 0° C., and neat allyl bromide (0.95 mL) was added. After 1 hour, 20 mL of an aqueous saturated ammonium chloride solution was added, and the mixture extracted with ethyl acetate, the extracts washed with water, brine, dried over anhydrous sodium sulfate, filtered and evaporated to afford the title compound as a colorless oil, 2.4 g. (HRMS calc'd 250.1004; found 250.1002).

2. Methyl 2,3-dihydro-6-fluoro-4-(2-(benzyloxyamino)ethyl)4H-1-benzopyran-4-carboxylate A solution of methyl 2,3-dihydro-6-fluoro-4-(2-propenyl)-4H-1-benzopyran-4-carboxylate (3.8 g) in 350 mL of a mixture of 10% saturated methanolic potassium hydrogen carbonate/90% dichloromethane was cooled to −78° C., and perfused with a mixture of ozone in dry oxygen until a faint blue color persisted. Dimethyl sulfide (10 mL) was added, and the mixture was allowed to warm to room temperature. The mixture was evaporated under reduced pressure, partitioned between ethyl acetate and water, and the organic layers dried over anhydrous sodium sulfate, filtered, and evaporated. The oily residue was dissolved in anhydrous pyridine (75 mL), and solid O-benzylhydroxylamine was added and the mixture stirred at room temperature for 15 hours, then concentrated in vacuo. The residue was dissolved in anhydrous methanol (150 mL), and solid sodium cyanoborohydride (3.5 g) was added portionwise over 3 hours, alternating with additions of 1N aqueous HCl to maintain the mixture at pH 3–5. Solid sodium acetate was added, and the mixture concentrated in vacuo, extracted with ethyl acetate, and the organic extract washed with water, brine, dried over anhydrous sodium sulfate, filtered and evaporated. The residue was chromatographed over silica gel, eluting with diethyl ether/hexane (2:1) to yield the title compound, 3.1 g.

| Mass spectrum: | calc'd for C₂₀H₂₂FNO₄ | 359.1533 |
| --- | --- | --- |
| | found | 359.1539 |

3. 1′-benzyloxy-2,3-dihydro-6-fluoro-spiro-(4H-1-benzopyran-4,3′-pyrrolidine)-2′-one To a solution of methyl 2,3-dihydro-6-fluoro-4-(2-(benzyloxyamino)ethyl)-4H-1-benzopyran-4-carboxylate (3.1 g) in anhydrous tetrahydrofuran at −78° C. was added a solution of 1-M lithium diisopropylamide (9.0 mL) in tetrahydrofuran. After 1 hour acetic acid (1 mL) was added, and the solution concentrated in vacuo. The residue was partitioned between ethyl acetate and 1N HCl, and organic layers washed with 1N HCl, saturated aqueous sodium bicarbonate, brine, dried over sodium sulfate, filtered and evaporated to afford the title compound as an oil, 2.9 g. (¹H NMR (CDCl₃, 60

MHz): 1.9–2.5 (m, 4H), 3.2–4.6 (m, 4H), 5.0 (s, 2H), 6.3–6.8 (m, 3H), 7.3–7.5 (m, 5H).

4. 1'-hydroxy-2,3-dihydro-6-fluoro-spiro-(4H-1-benzopyran-4,3'-pyrrolidine)-2'one A solution of 1'-benzyloxy-2,3-dihydro-6-fluoro-spiro-(4H-1-benzopyran-4,3'-pyrrolidine)-2'-one (1.4 g) in methanol (75 mL) containing 10% palladium on carbon (300 mg) was stirred vigorously under hydrogen gas (1 atm). After 18 hours, more palladium on carbon (300 mg) was added, and the mixture was then filtered after being stirred under hydrogen gas for a further 20 minutes. The filtrate was concentrated in vacuo, and the residue purified by silica gel chromatography, eluting with ethyl acetate, to afford the title compound as a white crystalline solid, 780 mg, m.p. 208°–209° C.

EXAMPLE 6

1. Benzyl (cis,trans)-2,3-dihydro-7-fluoro-2-methyl-4-(2-propenyl)-4H-1-benzopyran-4-carboxylate To a suspension of sodium hydride (600 mg) in dimethylformamide (45 mL) was added benzyl-7-fluoro-2-methylchromane-4-carboxylate (6.0 g) in dimethylformamide (30 mL). After evolution of hydrogen ceased, allyl bromide (2.1 mL) was added in one portion, and the mixture stirred at room temperature for 1 hour, then poured into ice/$H_2O$ (150 mL)/1N HCl (20 mL), extracted with ethyl acetate (3×100 mL) and the combined organic extracts washed with $H_2O$, brine, dried over $Na_2SO_4$, filtered and evaporated to yield the title compounds as an oil (6.9 gm, 1:1 mixture of cis/trans). (Rf=0.6, 2.1 hexane/diethyl ether, $SiO_2$)

2 Benzyl (cis, trans)-2,3-dihydro-7-fluoro-2-methyl-4-(2-benzyloxyaminoethyl)-4H-1-benzopyran-4-carboxylate A solution of benzyl (cis,trans)-2,3-dihydro-7-fluoro-2-methyl-4-(2-propenyl)-4H-1-benzopyran-4-carboxylate in dichloromethane (550 mL) and saturated methanolic potassium bicarbonate (150 mL) cooled to −78° C. was perfused with a mixture of ozone in oxygen until the blue color of ozone persisted and consumption of the starting olefin was complete as judged by thin layer chromatography (2:1 ethyl acetate/hexane on $SiO_2$) After purging with nitrogen, dimethyl sulfide (20 mL) was added, and the mixture allowed to warm to room temperature. After 2 hours, the mixture was concentrated under reduced pressure and the residue partitioned between diethyl ether (200 mL) and water. The organic layer was washed repeatedly with water, brine, dried over $Na_2SO_4$, filtered and concentrated under reduced pressure. The oily residue was dissolved in pyridine (100 mL), and solid O-benzylhydroxylamine hydrochloride (3.4 gm) added, and the mixture stirred at room temperature for 2 hours, then concentrated under reduced pressure. The residue was dissolved in ethyl acetate (200 mL) and washed with saturated NaHCO$_3$, brine, dried (Na$_2$SO$_4$), filtered and evaporated. The oily residue was then dissolved in tetrahydrofuran (150 mL)/H$_2$O (10 mL) and sodium cyanoborohydride (1.8 gm) added, followed by 1N aqueous HCl (30 mL). After 1 hour, additional sodium cyanoborohydride (1.8 gm) and 1N aqueous HCl (30 mL) were added, and the additions repeated again after an additional 1 hour. After 2.5 hours total reaction time, solid sodium acetate (10 g) was added and the mixture concentrated under reduced pressure. The residue was diluted with $H_2O$ (100 mL) saturated sodium bicarbonate (50 mL) and repeatedly extracted with ethyl acetate (3×150 mL). The combined organic extracts were washed with $H_2O$, brine, dried (Na$_2$SO$_4$), filtered and evaporated to yield an oily residue (9.2 g), which was purified by column chromatography (diethyl ether/hexane 2:1 over $SiO_2$) to yield the title compounds (6.0 g) (Rf=0.1, 2:1 hexane/diethyl ether, $SiO_2$).

3. Cis and trans 1'benzyloxy-2,3-dihydro-6-fluoro-2-methyl-spiro-(4H-1-benzopyran-4,3'-pyrrolidine)-2'-ones To a solution of benzyl (cis, trans)-2,3-dihydro-7-fluoro-2-methyl-4-(2-benzyloxyaminoethyl)-4H-1-benzopyran-4-carboxylate (6.0 g) in anhydrous tetrahydrofuran (150 mL) at −78° C. was added a solution of 1N lithium diisopropylamide (16.3 mL) in tetrahydrofuran. After 1 hour acetic acid (4 mL) was added, and the solution concentrated in vacuo. The residue was partitioned between ethyl acetate and 1N HCl, and the organic layers washed with water, brine, dried over sodium sulfate, filtered and evaporated to afford a crystalline solid, 5.2 g.

Crystallization from ethyl acetate/hexane gave a pure sample (1.1 g) of the chromatographically (diethyl ether/hexanes 2:1, $SiO_2$) more polar diastereomer. The mother liquors were concentrated under reduced pressure, and the residue purified by column chromatography (diethyl ether/hexanes 2:1, $SiO_2$) to afford a less polar diastereomer (1.75 g, m.p. 94°–95° C. from ethyl acetate/hexane) and an additional sample of the more polar diastereomer (700 mg, m.p. 143°–144° C. from ethyl acetate/hexane).

4. More polar diasteromer of 1'-hydroxy-2,3-dihydro-6-fluoro-2-methyl-spiro-(4H-1-benzopyran-4,3'-pyrrolidine)-2'one A solution of the more polar diastereomer of 1'-benzyloxy-2,3-dihydro-6-fluoro-2-methyl-spiro-(4H-1-benzopyran-4,3'-pyrrolidine)-2'-one (1.7 g) in methanol (75 mL) containing 10% palladium on carbon (350 mg) was stirred vigorously under hydrogen gas (1 atm). After 15 minutes, the mixture was filtered, and the filtrate was concentrated in vacuo. The title compound was obtained as needles following recrystallization from ethyl acetate hexanes (m.p. 205°–207° C., 840 mg).

5. The less polar diastereomer of 1'-hydroxy-2,3-dihydro-6-fluoro-2-methyl-spiro-(4H-1-benzopyran-4,3'-pyrrolidine)-2'one Prepared from the less polar diastereomer of 1'-benzyloxy-2,3-dihydro-6-fluoro-2-methyl-spiro-(4H-1-benzopyran-4,3'-pyrrolidine)-2'-one (700 mg) by the same procedures used for the preparation of the product of Example 6, part 4 from the more polar diastereomer of 1'-benzyloxy-2,3-dihydro-6-fluoro-2-methyl-spiro-(4H-1-benzopyran-4,3'-pyrrolidine)-2'-one, providing two apparent polymorphic crystalline forms, one (m.p. 132° C., 360 mg) obtained by crystallization of the crude product from ethyl acetate hexanes and a second by crystallization (ethyl acetate/hexanes) of material obtained by column chromatography of the mother liquors (m.p. 189°–190° C., 330 mg).

EXAMPLE 7

1. 2,3-dihydro-6-fluoro-2-(2-phenylethyl)-4H-1-benzopyran-4-one

Pyrrolidine (2.4 mL) was added to a solution of 2'-hydroxy-5'-fluoroacetophenone (15.1 g) and 3-phenylpropanal (13.2 mL) in toluene (30 mL), and the mixture heated under reflux in a Dean-Stark apparatus for 3 hours, cooled, diluted with ethyl acetate and washed with aqueous 1N HCl, aqueous 1N NaOH, $H_2O$, brine, dried ($Na_2SO_4$), filtered and evaporated, and the residue purified by column chromatography (6:1 hexane/diethyl ether, $SiO_2$) to yield 2,3-dihydro-6-fluoro-2-(2-phenylethyl)-4H-1-benzopyran-4-one (18 gm, Rf=0.3 4:1 hexane/diethyl ether).

2. Cis and trans 4-cyano-2,3-dihydro-6-fluoro-2-(2-phenylethyl)-4H-1-benzopyran 2,3-dihydro-6-fluoro-2-(2-phenylethyl)-4H-1-benzopyran-4-one (8.9 gm) was dissolved in anhydrous tetrahydrofuran, and toluenesulfonylmethylisocyanide (12.9 gm) added, followed by freshly prepared sodium ethoxide in ethanol (prepared from sodium (1.5 gm) in ethanol (60 mL) and the mixture stirred at room temperature overnight. The mixture was then concentrated in vacuo, and the residue partitioned between ethyl acetate and $H_2O$, and the organic layer washed with $H_2O$, brine, dried, filtered and evaporated. The residue was purified by column chromatography (2:1 hexanes/diethyl ether) to yield 4-cyano-2,3-dihydro-6-fluoro-2-(2-phenylethyl)-4H-1-benzopyran (2.7 gm, ir: 2250 $cm^{-1}$).

3. Cis and trans 2,3-dihydro-6-fluoro-2-(2-phenylethyl)-4H-1-benzopyran-4-carboxylic acid 2,3-dihydro-6-fluoro-4-cyano-2-(2-phenylethyl)-4H-1-benzopyran (2.7 gm) and solid KOH (2.7 gm) were suspended in ethylene glycol (100 mL) and heated under reflux for 1.5 hours, then poured onto ice/$H_2O$ (300 mL), and extracted with diethyl ether, and the organic extracts discarded. The aqueous layer was acidified to pH 1 with 6N HCl, and extracted with ethyl acetate, and the extracts washed with $H_2O$, brine, dried, filtered and evaporated to yield the title compound (2.9 gm, m.p. 105°-108° C.).

4. Cis and trans methyl 2,3-dihydro-6-fluoro-2-(2-phenylethyl)-4H-1-benzopyran-4-carboxylate Cis and trans 2,3-dihydro-6-fluoro-2-(2-phenylethyl)-4H-1-benzopyran-4-carboxylic acid (2.9 gm) was dissolved in methanol, cooled to 0° C., and the mixture saturated with gaseous HCl. After 24 hours, the mixture was concentrated in vacuo, and the residue partitioned between ethyl acetate and saturated sodium bicarbonate. The organic layer was washed with brine, dried ($Na_2SO_4$), filtered and evaporated. The residue was purified by column chromatography (2:1 hexane/diethyl ether, $SiO_2$) to yield the title compound (1.9 gm, Rf=0.3, 2:1 hexane/diethyl ether, $SiO_2$).

5. More polar diasteromer of 1-hydroxy-2,3-dihydro-6-fluoro-2-(2-phenylethyl)-spiro-(4H-1-benzopyran-4,3'-pyrrolidine)-2'one (m.p. 82°-84° C.)

Prepared from methyl 2,3-dihydro-6-fluoro-2-(2-phenylethyl)-4H-1-benzopyran-4-carboxylate by the same procedures used for the preparation of the product in Example 6, part 4 from methyl 2,3-dihydro-6-fluoro-4H-1-benzopyran-4-carboxylate, via intermediacy of the more polar diastereomer of 1'-benzyloxy-2,3-dihydro-6-fluoro-2-(2-phenylethyl)-spiro-(4H-1-benzopyran-4,3'-pyrrolidine)-2'-one (Rf=0.2, 1:1 diethyl ether/hexanes).

EXAMPLE 8

1. 2,3-dihydro-6-fluoro-2-propyl-4H-1-benzopyran-4-one

2'-hydroxy-5'-fluoroacetophenone (2 gm) in tetrahydrofuran (10 mL) was added dropwise to sodium hydride (600 mg), then ethyl butyrate (10 mL) was added. After 30 minutes, aqueous 1N HCl (50 mL) was added, and the mixture extracted with ethyl acetate, and the extracts washed with $H_2O$, saturated aqueous $NaHCO_3$, brine, dried ($Na_2SO_4$), filtered and evaporated. The residue was dissolved in dichloromethane (100 mL), and trifluoroacetic acid (7 mL) added, and after stirring overnight at room temperature, dichloromethane and saturated aqueous $NaHCO_3$ were added, and the layers separated. The organic layer was washed with $H_2O$, brine, dried ($Na_2SO_4$), filtered and concentrated in vacuo to yield 6-fluoro-2-propyl-4H-1-benzopyran-4-one (2.4 gm, Rf=0.4 1:1 diethyl ether/hexanes). This compound (9 gm) was dissolved in ethanol (250 mL) and sodium borohydride (1.6 gm) added, and the mixture heated under reflux. After 3.5 hours additional sodium borohydride (1.6 gm) added, and after 7 hours a further addition of sodium borohydride (1.6 gm) was made. After 10 hours more sodium borohydride (0.8 gm) was added and after 23 hours total reaction time the mixture was concentrated under reduced pressure, and partitioned between ethyl acetate and $H_2O$. The organic layer was washed with brine, dried ($Na_2SO_4$), filtered and evaporated to yield 4-hydroxy-2,3-dihydro-6-fluoro-2-propyl-4H-1-benzopyran-4-one (Rf=0.4 1:1 diethyl ether/hexanes). This material (10.8 gm) was dissolved in acetic acid (45 mL) and a solution of chromium trioxide (7.8 gm) in acetic acid (45 mL)/$H_2O$ (10 mL) was added dropwise. After one hour, the mixture was poured into ice/$H_2O$ (1L) and extracted with ethyl acetate. The extracts were washed with $H_2O$, saturated $NaHCO_3$, dried ($Na_2SO_4$), filtered and evaporated to yield the title compound (7.4 g, Rf=0.7, 1:1 diethyl ether/hexanes).

2. More polar diastereomer of 1'-hydroxy-2,3-dihydro-6-fluoro-2-(2-propyl)-spiro-(4H-1-benzopyran-4,3'-pyrrolidine)-2'one (m.p. 138°-140° C.)

Prepared from 2,3-dihydro-6-fluoro-2-propyl-4H-1-benzopyran-4-one via the intermediacy of the more polar diastereomer of 1'-benzyloxy-2,3-dihydro-6-fluoro-2-(2-propyl)-spiro-(4H-1-benzopyran-4,3'-pyrrolidine)-2'one (Rf=0.2, 1:1 diethyl ether/hexanes) using the same procedure for preparation of Example 7 from 2,3-dihydro-6-fluoro-2-(2-phenylethyl-4H-1-benzopyran-4-one.

3. Less polar diastereomer of 1'-hydroxy-2,3-dihydro-6-fluoro-2-(2-propyl)-spiro-(4H-1-benzopyran-4,3'-pyrrolidine)-2'-one (m.p. 109°–111° C.)

Prepared from 2,3-dihydro-6-fluoro-2-propyl-4H-1-benzopyran-4-one via the intermediacy of the less polar diasteromer of 1'-benzyloxy-2,3-dihydro-6-fluoro-2-(2-propyl)-spiro-(4H-1-benzopyran-4,3 '-pyrrolidine)-2'one (Rf=0.3, 1:1 diethyl ether/hexanes) using the same procedure as that used for preparation of Example 7 from 2,3-dihydro-6-fluoro-2-(2-phenylethyl)-4H-1-benzopyran-4-one.

EXAMPLE 9

1. Cis and trans 6,7-dichloro-2,3-dihydro-2-methyl-4H-1-benzopyran-4-carboxylic acid A mixture of 6,7-dichloro-2-methyl-4H-1-benzopyran-4-one (5 gm), cyanotrimethylsilane (3.5 mL), zinc iodide (670 mg) in dichloromethane (50 mL) was stirred at room temperature for 16 hours, then diluted with dichloromethane (200 mL), washed with saturated sodium bisulfite, saturated sodium bicarbonate, brine, dried ($Na_2SO_4$), filtered and concentrated in vacuo. The residue was added to concentrated $H_2SO_4$ (30 mL) in one portion at room temperature, and after 10 minutes, poured onto ice/$H_2O$, extracted with ethyl acetate and the organic layer washed with $H_2O$, brine, dried ($MgSO_4$), filtered and concentrated under reduced pressure. The residue was then dissolved in ethanol (50 mL), and sodium borohydride (380 mg) added. After 15 minutes, the mixture was concentrated in vacuo, and the residue partitioned between ethyl acetate and $H_2O$. The organic extracts were washed with $H_2O$, brine, dried over $Na_2SO_4$, filtered, and evaporated. The residue was then suspended in ethylene glycol (100 mL), and solid KOH (5.4 gm) added. After heating under reflux for 2.5 hours, the mixture was cooled, and diluted with $H_2O$ (300 mL), extracted with dichloromethane, and the organic extract back-washed with aqueous 1N KOH. The combined aqueous layers were acidified with concentrated HCl to pH 1, extracted with ethyl acetate, and the organic extracts washed with water, brine, dried ($MgSO_4$), filtered and concentrated in vacuo. The residue was dissolved in dichloromethane and decolorized with activated charcoal, filtered, concentrated vacuo, and crystallized from hexanes to yield the title compound (1.2 gm, m.p. 108°–110° C.).

2. Methyl cis and trans 6,7-dichloro-2,3-dihydro-2-methyl-4H-1-benzopyran-4-carboxylate cis and trans 6,7-dichloro-2,3-dihydro-2-methyl-4H-1-benzopyran-4-carboxylic acid (27.4 gm) was dissolved in methanol (500 mL), cooled to 0° C., and the solution saturated with gaseous HCl, then allowed to warm to room temperature. After 16 hours, the mixture was concentrated under reduced pressure, and the residue dissolved in ethyl acetate, washed with saturated sodium bicarbonate, brine, dried ($MgSO_4$), filtered and evaporated. The residue was vacuum distilled (Kugelrohr, 150° C./1.5 mm Hg) to yield the title compound (20 g, Rf=0.5, 1.1 diethyl ether/hexanes, $SiO_2$).

3. More polar diastereomer of 1'-hydroxy-2,3-dihydro-6,7-dichloro-2-methylspiro-(4H-1-benzopyran-4,3'-pyrrolidine)-2'one (m.p. 118°–121° C.)

Prepared from methyl cis and trans 6,7-dichloro-2,3-dihydro-2-methyl-4H-1-benzopyran-4-carboxylate in the same manner as the product of Example 6, part 4 from more polar diastereomer of 1'-benzyloxy-2,3-dihydro-6-fluoro-2-methyl-spiro-(4H-1-benzopyran-4,3'-pyrrolidine)-2'-one, via intermediacy of methyl cis and trans 6,7-dichloro-2,3-dihydro-2-methyl-4-(2-propenyl)-4H-1-benzopyran-4carboxylate (Rf=0.6, 1:1 diethyl ether/hexanes, $SiO_2$), methyl cis and trans 6,7-dichloro-2,3-dihydro-2-methyl-4-(2-benzyloxyaminoethyl)-4H-1-benzopyran-4-carboxylate (Rf=0.4, 1:1 diethyl ether/hexanes, $SiO_2$), and the more polar diasteromer of 1'-benzyloxy-2,3-dihydro-6,7-dichloro-2-methyl-spiro-(4H-1-benzopyran-4,3'-pyrrolidine)-2'one (Rf=0.7, diethyl ether, $SiO_2$).

4. Less polar diastereomer of 1'-hydroxy-2,3-dihydro-6,7-dichloro-2-methylspiro-(4H-1-benzopyran-4,3'-pyrrolidine)-2'one (m.p. 82°–85° C.)

Prepared in the same manner as Example 9, part 3 via intermediacy of the less polar diastereomer of 1'-benzyloxy-2,3-dihydro-6,7-dichloro-2-methyl-spiro(4H-1-benzopyran-4,3'-pyrrolidine)-2'one (Rf=0.8, diethyl ether, $SiO_2$).

EXAMPLE 10

1. 4-carboxymethylene-2,3-dihydro-6-fluoro-4H-1-benzopyran-4-carboxylic acid A solution of methyl 6-fluorochromane-4-carboxylate (600 mg) in anhydrous N,N-dimethylformamide was added to a suspension of sodium hydride (80 mg) in anhydrous N,N-dimethylformamide under nitrogen. After gas evolution ceased, the mixture was cooled to 0° C., and neat ethyl bromoacetate (0.4 mL) was added. After 1 hour, aqueous 1N HCl (50 mL) was added, and the mixture extracted with ethyl acetate, the extracts washed with water, brine, dried over anhydrous sodium sulfate, filtered and evaporated. The residue was dissolved in ethylene glycol (50 mL) and after addition of solid KOH (0.6 g), heated under reflux for 2.5 hours, then cooled, diluted with $H_2O$ (100 ml) extracted with ethyl acetate, and the organic layer discarded after washing with aqueous 5N KOH. The combined aqueous layers were acidified with concentrated HCl to pH 1 and extracted repeatedly with ethyl acetate. The combined extracts were washed with water, brine, dried ($Na_2SO_4$), filtered and concentrated under reduced pressure. Crystallization of the residue from ethyl acetate hexanes afforded the title compound (m.p. 211°–212° C., 150 mg).

2. 1'-hydroxy-2,3-dihydro-6-fluoro-spiro-(4H-1-benzopyran-4,3'-pyrrolidine-2'one The diacid (1.02 gm) was dissolved in acetic anhydride (50 mL) and heated under reflux for 3 hours. After concentration under reduced pressure, column chromatography (1:1 diethyl ether/hexane, $SiO_2$), the resulting anhydride was dissolved in methanol (5 mL) and a solution of hydroxylamine in methanol, prepared from hydroxylamine hydrochloride (310 mg), sodium methoxide (240 mg) in methanol (10 mL), was added. After 3 hours, the mixture was concentrated in vacuo. The residue was then heated in xylenes under reflux for 3.5 hours, and after removal of solvent under reduced pressure, the residue was crystallized (ethyl acetate/hexanes) to yield the title compound (m.p. 190°–192° C., 155 mg).

EXAMPLE 11

1. Cis/trans-6-fluoro-4-methoxycarbonyl-2-methyl-1-tetralone

To a solution of methyl 3-fluorophenylacetate (prepared from 3 fluorophenylacetic acid (Aldrich Chem. Co., Madison, Wis.) via esterification with methanol catalyzed by gaseous HCl) in anhydrous N,N-dimethylformamide (40 mL) warmed to 70° C. was added methyl methacrylate (5.8 mL) and potassium tertbutoxide (0.55 gm). After 15 minutes, aqueous 1N HCl (75 mL) was added, and the mixture extracted with diethyl ether. The organic extracts were washed with $H_2O$, brine, dried ($Na_2SO_4$, filtered and evaporated. The residue was dissolved in concentrated $H_2SO_4$ (80 mL)/$H_2O$ (20 mL), and warmed to 70° C. for 3 hours, then poured onto crushed ice, and the mixture extracted with ethyl acetate. The extracts were washed with $H_2O$, brine, dried ($Na_2SO_4$, filtered and evaporated. The oily residue was dissolved in methanol (250 mL), and the solution saturated with gaseous HCl. After 30 minutes, the mixture was purged with nitrogen, and concentrated under reduced pressure. The oily residue was partitioned between $H_2O$ (500 mL), and ethyl acetate, and the organic layer washed with water, brine, dried ($Na_2SO_4$), filtered and concentrated in vacuo to yield the title compound (10.9 gm, Rf (1:1 diethyl ether/$SiO_2$)=0.4).

2. Cis/trans-6-fluoro-4-methoxycarbonyl-2-methyl-4-(2-propenyl)-1-tetralone

A solution of cis/trans-6-fluoro-4-methoxycarbonyl-2-methyl-1-tetralone (3.6 g) in anhydrous N,N-dimethylformamide (20 mL) was added dropwise to a suspension of sodium hydride (400 mg) in anhydrous N,N-dimethylformamide (70 mL) and the mixture stirred at 0° C. for 15 minutes. Neat allyl bromide (1.4 mL) was then added, and after 20 minutes, aqueous 1N HCl (50 mL) was added, the mixture extracted with ethyl acetate, and the organic layers washed with $H_2O$, brine, dried ($Na_2SO_4$) filtered and evaporated to afford the title compound (4.2 g, Rf (1:1 diethyl ether/$SiO_2$)=0.5).

3. Cis/trans-6-fluoro-4-methoxycarbonyl-2-methyl-4-(2-benzyloxyaminoethyl)-1-tetralone Prepared from cis/trans-6-fluoro-4-methoxycarbonyl-2-methyl-4-(2-propenyl)-1-tetralone as per the procedure outlined for Example 6, part 4 above, (Rf (1:1 diethyl ether/$SiO_2$)=0.3).

4. Cis and trans 1'-benzyloxy-6-fluoro-2-methyl-spiro-(1-oxotetralin-4,3'-pyrrolidine)-2'ones Prepared from cis/trans-6-fluoro-4-methoxycarbonyl-2-methyl-4-(2-benzyloxyaminoethyl)-1-tetralone as per the procedure outlined for Example 6, part 4 above. The individual diastereomers were isolated by column chromatography (3:1 diethyl ether/hexanes, $SiO_2$) yielding a less polar diastereomer (m.p. 128°–130° C.) and a more polar diastereomer (m.p. 110°–112° C.).

5. 1'-hydroxy-6-fluoro-2-methyl-spiro-(1-oxotetralin-4,3'-pyrrolidine)-2'-one A solution of the more polar diastereomer of cis and trans 1'-benzyloxy-6-fluoro-2-methyl-spiro-(1-oxotetralin-4,3'-pyrrolidine)-2'-one in methanol (30 mL) containing 10% palladium on carbon (80 mg) was stirred vigorously under hydrogen gas (1 atm). After 25 minutes the mixture was filtered and the filtrate was concentrated in vacuo. Trituration with diethyl ether yielded the title compound as white crystalline solid, 137 mg, (m.p. 106°–108° C.).

EXAMPLE 12

1. 6,7-dichloro-4H-1-benzopyran-4-carboxylic acid

To a solution of 2-trimethylsilyl-1,3-dithiane in anhydrous tetrahydrofuran (500 mL) at −78° C. under nitrogen was added 2.5M n-butyllithium in hexane (64 mL), and the mixture then allowed to warm to 0° C. After 2 hours, the mixture was cooled to −78° C. and a solution of 6,7-dichloro-4H-1-benzopyran-4-one in anhydrous tetrahydrofuran (150 mL) added dropwise. The mixture was then allowed to warm to room temperature. After 16 hours, the solvent was removed under reduced pressure, and the residue partitioned between ethyl acetate and $H_2O$, and organic extract washed with $H_2O$, brine, dried ($Na_2SO_4$), filtered and evaporated. The residue was dissolved in a mixture of acetic acid (750 mL), $H_2O$ (375 mL) and trifluoroacetic acid (15 mL) and heated under reflux for 20 hours, then cooled and poured into ice/$H_2O$ (2.5 L). The mixture was extracted with ethyl acetate and the organic extracts washed with water, saturated $NaHCO_3$, brine, dried ($Na_2SO_4$), filtered and evaporated. The residue was suspended in ethanol (800 mL)/$H_2O$ (400 mL), solid KOH (38 g) added, and the mixture heated under reflux for 1.5 hours. After concentration under reduced pressure, the mixture was diluted with $H_2O$ (600 mL), extracted with diethyl ether, and the ether extracts discarded. The aqueous layer was acidified to pH 1 with concentrated HCl, and extracted with ethyl acetate, and the extracts washed with water, brine, dried ($Na_2SO_4$), filtered and evaporated. Trituration of the solid residue with boiling hexane yielded the title compound (16.8 gm, m.p. 114°–117° C.).

2. Benzyl 6,7-dichloro-4H-1-benzopyran-4-carboxylate

A mixture of 6,7-dichloro-4H-1-benzopyran-4-carboxylic acid (16.8 gm), tetra (N-butyl)ammonium hydrogensulfate (23 gm), benzyl bromide (9.7 mL), saturated sodium bicarbonate (100 mL) and dichloromethane (100 mL) were stirred vigorously at room temperature for 14 hours, then diluted with dichloromethane, and the organic layer separated, washed with saturated sodium bicarbonate, water, brine, dried ($MgSO_4$), filtered and evaporated. The residue was purified by column chromatography (2:1 dichloromethane/hexanes, $SiO_2$) to afford the title compound (11.8 gm, Rf=0.3 (2:1 dichloromethane/hexanes, $SiO_2$).

It should be understood that the invention is not limited to the particular embodiments shown and described herein, but that various changes and modifications may be made without departing from the spirit and scope of this novel concept as defined by the following claims.

What is claimed is:

1. A compound of the formula

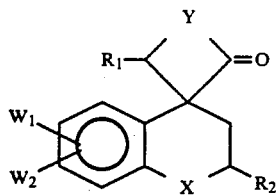

Formula I wherein
Y is

X is —O— or

$R_1$ and $R_2$ are each independently H, alkyl $C_1$-$C_6$, aryl or arylalkyl ($C_1$-$C_6$);

$W_1$ and $W_2$ are each independently hydrogen, halogen or nitro; and the pharmaceutically acceptable base addition salts thereof.

2. A compound of claim 1 wherein X is

3. A pharmaceutical composition for the control of chronic diabetic complications in mammals which comprises an effective amount of a compound of claim 1 in a pharmaceutically acceptable carrier.

4. A method of controlling chronic diabetic complications which comprises administering to a mammal suffering from chronic diabetes a chronic diabetic complication controlling amount of a compound of claim 1.

5. A compound of claim 1 wherein X is —O—.

6. A compound of claim 5 wherein $W_1$ and $W_2$ are each independently hydrogen or halogen and $R_1$ and $R_2$ are each independently H or alkyl($C_1$-$C_6$).

7. A compound of claim 6 wherein $R_1$ is hydrogen or methyl, $R_2$ is hydrogen or methyl, and either $W_1$ and $W_2$ are each chlorine in position 6 and 7 respectively or $W_1$ is hydrogen and $W_2$ is fluorine in position 6.

* * * * *